(12) United States Patent
Lake et al.

(10) Patent No.: US 11,105,231 B1
(45) Date of Patent: Aug. 31, 2021

(54) VEHICLE LIQUID MONITORING SYSTEM AND METHOD

(71) Applicant: UIPCO, LLC, San Antonio, TX (US)

(72) Inventors: Zachery C. Lake, The Colony, TX (US); Kade L. Scott, Scottsdale, AZ (US); Benjamin D. Ethington, Savannah, TX (US); Matthew T. Flachsbart, Grapevine, TX (US); Cory A. Matheson, Celina, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 170 days.

(21) Appl. No.: 16/204,426

(22) Filed: Nov. 29, 2018

Related U.S. Application Data

(60) Provisional application No. 62/593,201, filed on Nov. 30, 2017.

(51) Int. Cl.

| | | |
|---|---|---|
| *F01M 11/12* | (2006.01) | |
| *G01F 23/04* | (2006.01) | |
| *G01N 33/28* | (2006.01) | |
| *F01M 11/10* | (2006.01) | |

(52) U.S. Cl.
CPC ............. *F01M 11/12* (2013.01); *G01F 23/04* (2013.01); *G01N 33/2888* (2013.01); *F01M 2011/1406* (2013.01); *F01M 2011/148* (2013.01); *F01M 2011/1453* (2013.01); *F01M 2011/1466* (2013.01); *F01M 2011/1473* (2013.01)

(58) Field of Classification Search
CPC .... G01F 23/04; G01N 33/2888; F01M 11/12; F01M 2011/14; F01M 2011/148; F01M 2011/1473; F01M 2011/1466; F01M 2011/1453
See application file for complete search history.

(56) References Cited

U.S. PATENT DOCUMENTS

| | | | |
|---|---|---|---|
| 7,581,434 B1* | 9/2009 | Discenzo | G01N 33/2888 73/53.01 |
| 2006/0135374 A1* | 6/2006 | Cooper | F16C 33/106 508/150 |
| 2007/0057593 A1* | 3/2007 | Ito | H02K 21/24 310/216.066 |
| 2019/0162687 A1* | 5/2019 | Best | F02C 7/00 |

FOREIGN PATENT DOCUMENTS

JP 2014007798 A * 1/2014 ............. H02N 2/185

* cited by examiner

*Primary Examiner* — Paul M. West
(74) *Attorney, Agent, or Firm* — Fletcher Yoder P.C.

(57) ABSTRACT

A vehicle liquid testing system includes a liquid testing apparatus with a form factor of a dipstick. The system includes a sensor that detects a property of a fluid in a vehicle and emits a signal indicative of the property. A transmitter receives the signal from the sensor and transmits the signal. A controller receives the signal from the transmitter and compares the signal from the sensor to a threshold level to determine a condition of the fluid.

20 Claims, 5 Drawing Sheets

VEHICLE LIQUID MONITORING SYSTEM AND METHOD

CROSS-REFERENCE TO RELATED APPLICATION

This application claims benefit of and priority to U.S. Provisional Application No. 62/593,201, entitled "Vehicle Liquid Monitoring System and Method," filed on Nov. 30, 2017, which is hereby incorporated by reference for all purposes.

BACKGROUND

This section is intended to introduce the reader to various aspects of art that may be related to various aspects of the presently described embodiments. This discussion is believed to be helpful in providing the reader with background information to facilitate a better understanding of the various aspects of the present embodiments. Accordingly, it should be understood that these statements are to be read in this light, and not as admissions of prior art.

The majority of vehicles driven today include an internal combustion engine. The internal combustion engine produces power by combusting a fuel, typically gasoline or diesel. In order to combust the fuel, the fuel is mixed with air and injected into a piston cylinder. The piston cylinder compresses the fuel air mixture, which is ignited either by a spark in a gasoline engine or by compression in a diesel engine. Ignition of the fuel air mixture creates a pressure wave that then drives the piston, while simultaneously generating significant amounts of thermal energy. These moving parts are lubricated to keep the engine properly operating. More specifically, lubrication of the engine blocks engine seizure, reduces friction, and reduces thermal energy buildup that may cause premature wear of engine components. Vehicles using internal combustion engines therefore include fluid systems to lubricate and cool various components on the vehicle.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In an embodiment, a vehicle liquid testing system includes a liquid testing apparatus with a form factor of a dipstick. The liquid testing apparatus is inserted into a dipstick conduit of a vehicle. The liquid testing apparatus includes a sensor that detects a property of a fluid in the vehicle and emits a signal indicative of the property. A transmitter receives the signal from the sensor and transmits the signal.

In another embodiment, a vehicle liquid testing system includes a liquid testing apparatus. The liquid testing apparatus includes a sensor that detects a property of a fluid in a vehicle and emits a signal indicative of the property. A transmitter receives the signal from the sensor and transmits the signal. A controller receives the signal from the transmitter and compares the signal from the sensor to a threshold level to determine a condition of the fluid.

In another embodiment, a liquid testing apparatus has a form factor of a dipstick. The liquid testing apparatus includes a sensor that detects a property of a fluid in a vehicle and emits a signal indicative of the property. A controller receives the signal from the sensor and compares the signal from the sensor to a threshold level to determine a condition of the fluid. The apparatus includes a power source that powers the sensor and/or the controller.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
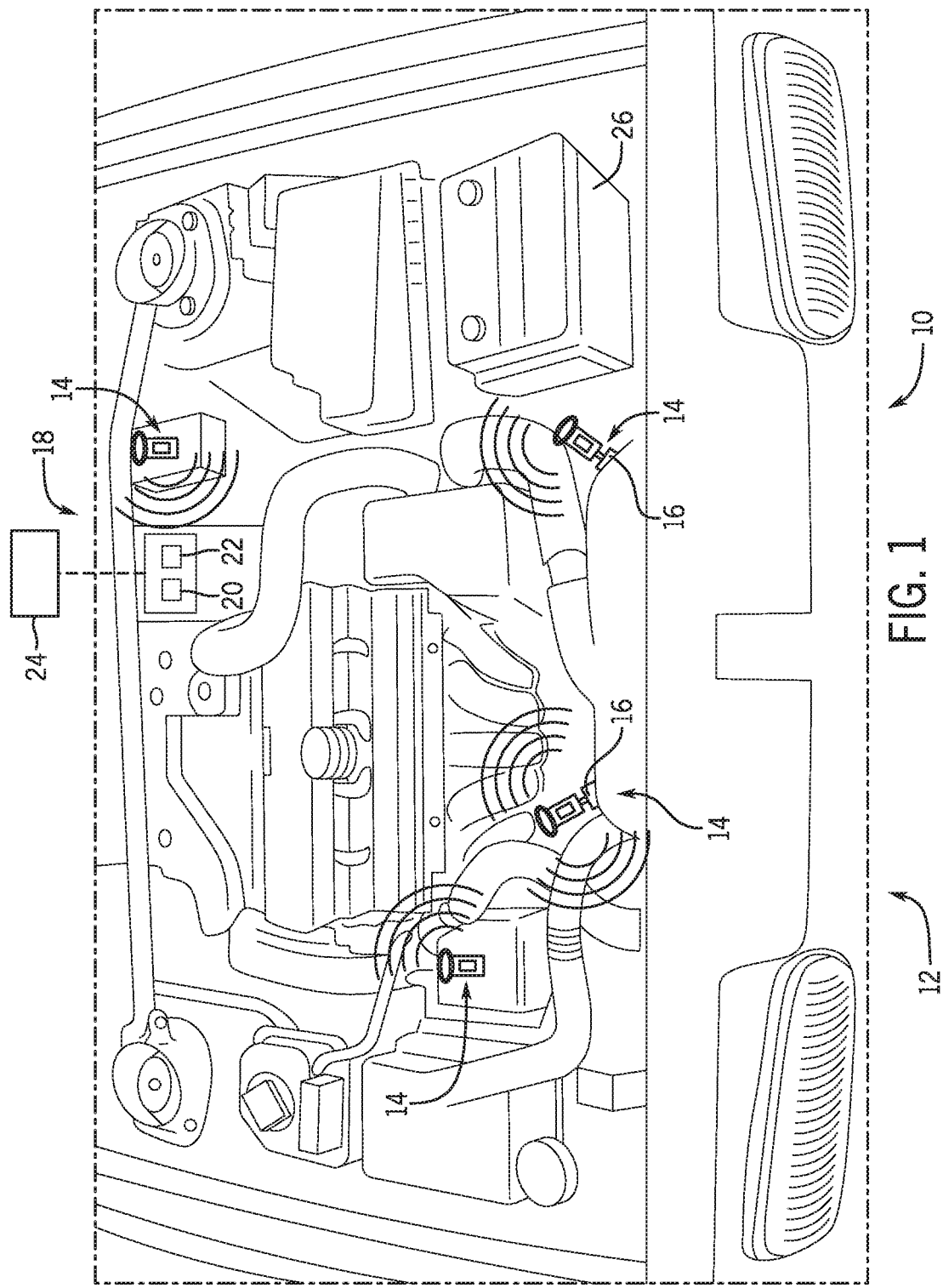
FIG. 1 illustrates an overhead perspective view of a vehicle engine with a vehicle liquid testing system, in accordance with embodiments described herein.

Reference will now be made in detail to specific embodiments illustrated in the accompanying drawings and figures. In the following detailed description, numerous specific details are set forth in order to provide a thorough understanding of the disclosure. However, it will be apparent to one of ordinary skill in the art that embodiments may be practiced without these specific details. In other instances, well-known methods, procedures, components, have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first object could be termed a second object, and, similarly, a second object could be termed a first object, without departing from the scope of the present disclosure.

The terminology used herein is for the purpose of describing particular embodiments only and is not intended to be limiting. As used in the description and the appended claims, the singular forms "a," "an" and "the" are intended to include the plural forms as well, unless the context clearly indicates otherwise. It will also be understood that the term "and/or" as used herein refers to and encompasses any and possible combinations of one or more of the associated listed items. It will be further understood that the terms "includes," "including," "comprises" and/or "comprising," when used in this specification, specify the presence of stated features, integers, steps, operations, elements, and/or components, but do not preclude the presence or addition of one or more other features, integers, operations, elements, components, and/or groups thereof. Further, as used herein, the term "if" may be construed to mean "when" or "upon" or "in response to determining" or "in response to detecting," depending on the context As explained above, the internal combustion engine produces power by combusting a fuel, typically gasoline or diesel. The combustion of the fuel creates thermal energy and drives movement of various engine parts, such as pistons, the crankshaft, the camshaft, and the transmission. These moving parts are lubricated to keep the vehicle properly operating. More specifically, lubrication of engine parts blocks engine seizure, reduces friction, and reduces thermal energy buildup that may cause premature wear of engine components. Vehicles using internal combustion engines therefore include various fluids to lubricate and/or cool components on the vehicle. These fluids may include motor oil, automatic transaxle oil, coolant, and power steering fluid.

During operation, these lubricating fluids are typically pumped with a pump through various passages in the engine, transmission, and other systems. For example, various passages in the engine block may distribute oil to various parts of the engine such as the pistons, bearings, and valves. As these fluids flow through and around components of the vehicle, they reduce friction, reduce heat generation, and protect various components of the vehicle.

Over time, these vehicle fluids may break down from thermal energy, contamination, etc. For this reason, the vehicle fluids are replaced on a regular basis. Current methods for determining when to change a vehicle's fluids may be done manually with what is colloquially referred to as a "dipstick." The dipstick is a rod that enables a user to check oil levels, transmission fluid levels, power steering fluid levels, coolant levels, and brake fluid levels. The dipstick may also allow a user to visually inspect and/or touch a sample of fluid that clings to an end of the dipstick. Information provided by the dipstick is valuable in that it enables the user to visually determine if there is an adequate supply of vehicle fluid as well as whether the fluid has degraded and is therefore incapable of providing adequate protection. Another method of determining when to change vehicle fluids may be done by monitoring mileage driven since the last change. For example, a user may replace the engine oil after driving 7,500 miles regardless of the condition of the oil. Unfortunately, many drivers fail to adequately monitor fluid levels in their vehicles due to the cumbersome and typically dirty task of manually checking the fluid. Moreover, visual inspection of the vehicle fluids may not accurately determine the condition of the vehicle fluids such as the presence of chemicals and particulate.

FIG. 1 illustrates an overhead perspective view of a vehicle engine 10 with a liquid testing system 12 (e.g., vehicle liquid testing system). In operation, the liquid testing system 12 enables automatic as well as continuous testing/monitoring of one or more vehicle fluids in the engine 10. In other words, the liquid testing system 12 may enable a user to determine the level and/or quality of the engine oil, automatic transaxle fluid, coolant, power steering fluid, and brake fluid without manually checking a dipstick. The liquid testing system 12 may include one or more liquid testing apparatuses 14 that contact respective fluids stored on the vehicle 10.

In some engines 10, the engine 10 may include conduits 16 that receive dipsticks. For example, the engine 10 may include a conduit 16 that leads to chamber containing motor oil or automatic transaxle fluid. The liquid testing apparatus 14 may have a form factor of a dipstick. In other words, certain dimensions of the liquid testing apparatus 14 correspond to the dimensions of a traditional dipstick so that the liquid testing apparatus 14 can be positioned in place of a traditional dipstick and coordinate with other features (e.g., the conduit 16) designed to coordinate with the traditional dipstick. Accordingly, vehicles may be retrofitted with the liquid testing system 12 by removing the original dipstick and replacing it with the liquid testing apparatus 14.

In order to detect the quality of the fluid as well as fluid levels, the liquid testing apparatus 14 may include multiple sensors capable of detecting particulates, viscosity, temperature, oil level, flow rate, contamination (e.g., chemical contamination), etc. As the liquid testing apparatus 14 senses the condition of the fluid, the liquid testing apparatus 14 transmits signals to one or more controllers 18. These controllers 18 may be located on the vehicle 10, on the liquid test apparatus (i.e., dipstick), and/or remotely located (e.g., car repair shop). For example, a mechanic may insert the liquid testing apparatus 14 into the engine during a routine checkup of the vehicle.

In the illustrated embodiment, the controller 18 includes a processor 20, such as the illustrated microprocessor, and a memory device 22. The controller 18 may also include one or more storage devices and/or other suitable components. The processor 20 may be used to execute software, such as software for comparing electrical signals from the liquid testing apparatus 14 to threshold levels for determining a fluid level and/or quality. Moreover, the processor 20 may include multiple microprocessors, one or more "general-purpose" microprocessors, one or more special-purpose microprocessors, and/or one or more application specific integrated circuits (ASICS), or some combination thereof. For example, the processor 20 may include one or more reduced instruction set (RISC) processors.

The memory device 22 may include a volatile memory, such as random access memory (RAM), and/or a nonvolatile memory, such as read-only memory (ROM). The memory device 22 may store a variety of information and may be used for various purposes. For example, the memory device 22 may store processor executable instructions (e.g., firmware or software) for the processor 20 to execute, such as instructions for comparing one or more signals from the liquid testing apparatus 14 to threshold levels for determining a fluid level and/or quality. The storage device(s) (e.g., nonvolatile memory) may include ROM, flash memory, a hard drive, or any other suitable optical, magnetic, or solid-state storage medium, or a combination thereof. The storage device(s) may store data, instructions, and any other suitable data.

In operation, the liquid testing apparatus 14 uses one or more sensors to detect one or more properties of a fluid inside of the vehicle/engine 10. As the sensors detect these properties, the liquid testing apparatus 14 transmits signals indicative of those properties to one or more controllers 18. The transmission of the signals may be done through wired networks (e.g., cables) and/or through wireless networks (e.g., Wi-Fi, Bluetooth, cellular). The controllers 18 then determine the quality of the fluid and/or level of the fluid by comparing the detected property to a threshold level/condition.

For example, if one of the sensors on the liquid testing apparatus 14 is a temperature sensor, the controller 18 compares the detected temperature of the fluid and compares it to a threshold temperature. If the temperature of the fluid (e.g. motor oil) is greater than the threshold temperature, the controller 18 may emit/transmit a warning signal to a user interface within the vehicle to warn the driver/operator of a problem. In another example, the liquid testing apparatus 14 may include a particulate sensor capable of detecting one or more particulates such as metal pieces, dirt, sludge, etc. in the fluid. This information may then be transferred to the controller 18 where it is compared against a threshold level of particulate matter for properly operating fluid. If the amount of particulate in the fluid is greater than a threshold level, the controller 18 may again emit/transmit a warning signal to a user interface indicating that the fluid is losing its ability to lubricate and/or cool engine components (i.e., particulate buildup may be due to wear of engine components). Other sensors used by the liquid testing system 12 may include viscosity sensors, flow rate sensors, chemical sensors, etc. that likewise measure a particular characteristic of the fluid that is then compared to a threshold level by the controller 18.

As the sensors detect the condition of the fluid, the information is transmitted directly from the liquid testing apparatus 14 to the controller 18. In this way, the liquid testing system 12 is able to continuously monitor the fluid and advise/warn the driver and/or mechanic of any potential problems before excessive wear of engine parts. In some embodiments, the controller 18 may transmit information about one or more fluids (e.g., fluid condition) to one or more electronic devices 24. The electronic device 24 may be a monitor on the vehicle (e.g., dashboard monitor, dashboard screen), a mobile electronic device (e.g., cellphone, tablet, laptop), or another computer (e.g., mechanic's computer). The transmitted information displayed on the electronic device 24 may be technical and/or generic. For example, generic information may include an estimated mileage until the next fluid change, estimated drive time until the next fluid change, fluid levels (e.g., high, low, just right). Examples of more technical information that may be displayed may include viscosity, particulate count, acidity, sludge content, detergent content, additive content (e.g., antiwear, dispersants, viscosity improvers), among others.

In some embodiments, the liquid testing apparatus 14 may power the sensors using an external power source such as a battery 26 and/or alternator. In some embodiments, the liquid testing apparatus 14 may power the sensors using a power generator on the liquid testing apparatus 14 such as piezoelectric generators, etc. And in still other embodiments, the liquid testing apparatus 14 may receive power from both a power generator on the liquid testing apparatus 14 as well as from a battery 26 and/or alternator. Depending on the power generation capabilities of the power generator on the liquid testing apparatus 14, the liquid testing apparatus 14 may also provide power to the battery 26 (i.e., recharge).

Figure 2:
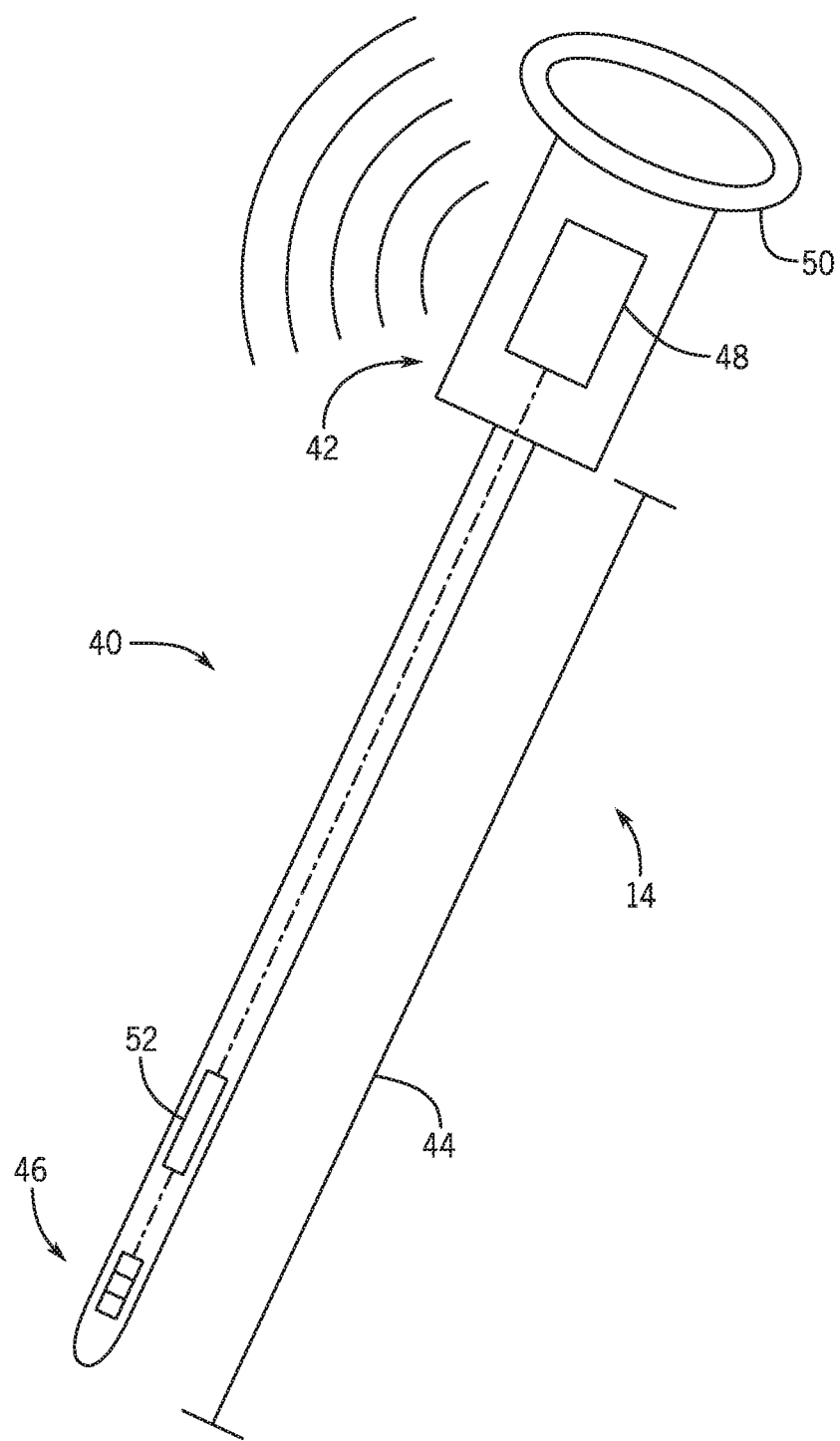
FIG. 2 illustrates a perspective view of a liquid testing apparatus having a form factor of a traditional dipstick, in accordance with embodiments described herein.

FIG. 2 illustrates a perspective view of an embodiment of a liquid testing apparatus 14 having a form factor of a dipstick. The liquid testing apparatus 14 includes a shaft 40 coupled to a handle/housing portion 42. The shaft 40 defines a length 44 that enables the liquid testing apparatus 14 to extend through a conduit 16 to enable the sensors 46 to contact a fluid within a compartment (e.g., oil pan). In particular, the shaft 40 has a form factor of a dipstick to facilitate engagement with traditional ports (e.g., the conduit 16) for dipsticks, which facilitates retrofitting with traditional vehicles. While the handle/housing portion 42 includes one or more transmitters 48 capable of transmitting signals from the sensors 46 to the controller(s) 18. In some embodiments, the liquid testing apparatus 14 may include a ring 50 that facilitates retrieval of the liquid testing apparatus 14 from the conduit 16. For example, the liquid testing apparatus 14 may be used by a mechanic to test the condition of a fluid in the engine 10 during periodic maintenance and the ring 50 may facilitate placement and retrieval of the liquid testing apparatus 14 from the conduit 16 or other compartment. The ring 50 may similarly be used by drivers to facilitate retrieval and placement of the liquid testing apparatus 14. For example, some drivers may desire to physically view the fluid and/or verify the fluid levels in the engine 10 in combination with receiving electronic feedback from the sensors 46.

Some of the possible sensors 46 on the liquid testing apparatus 14 include temperature sensors, flow rate sensors, contamination sensors (e.g. chemical sensors), particulate sensors, viscosity sensors, fluid level sensors, etc. Each of these sensors 46 provides feedback regarding the quality of the fluid enabling the liquid testing system 12 to alert a driver and/or mechanic to the development of potential problems in the engine 10 as well as alert the driver/mechanic that the fluid needs to be changed. For example, a temperature sensor may indicate whether the fluid is operating at a temperature that will result in rapid degradation of the fluid, thus enabling the driver to investigate the cause before excess wear on engine parts occurs. A contamination sensor may also provide useful feedback by detecting undesirable chemicals in the fluid (e.g., acids in motor oil). An excess concentration of these chemicals may similarly result in excess wear on engine parts. Particulate sensors detect particulates such as metal particulate, dirt, sludge, etc. in the fluid. The detection of metal and/or other particulate in the fluid may indicate that the fluid is not properly lubricating and thus friction between metal parts is beginning to wear the parts. The detection of sludge may also indicate excessive use of the fluid (e.g., sludge may be created when oil breaks down). Viscosity sensors detect the viscosity of the fluid. Over time, a fluid may break down due to the harsh operating conditions within the engine 10. As the fluid breaks down, the viscosity of the fluid may change. For example, a less viscous oil flows more easily and may be less capable of coating and lubricating engine parts. A fluid level sensor detects the amount of circulating fluid in the engine 10. Low levels of a fluid may reduce lubrication of engine parts and/or the ability of the fluid to cool parts of the engine. Accordingly, detecting low levels of fluid circulating through the engine may block premature wear of engine parts.

In one embodiment, in order to power these sensors 46 and the transmitter 48 that transmits the information to a controller 18, the liquid testing apparatus 14 includes a power generator 52. In some embodiments, the power generator 52 may also provide power to the vehicle, for example by recharging the battery 26 (seen in FIG. 1). The types of power generators 52 will be discussed in more detail below, but may include piezoelectric generators and turbines.

Figure 3:
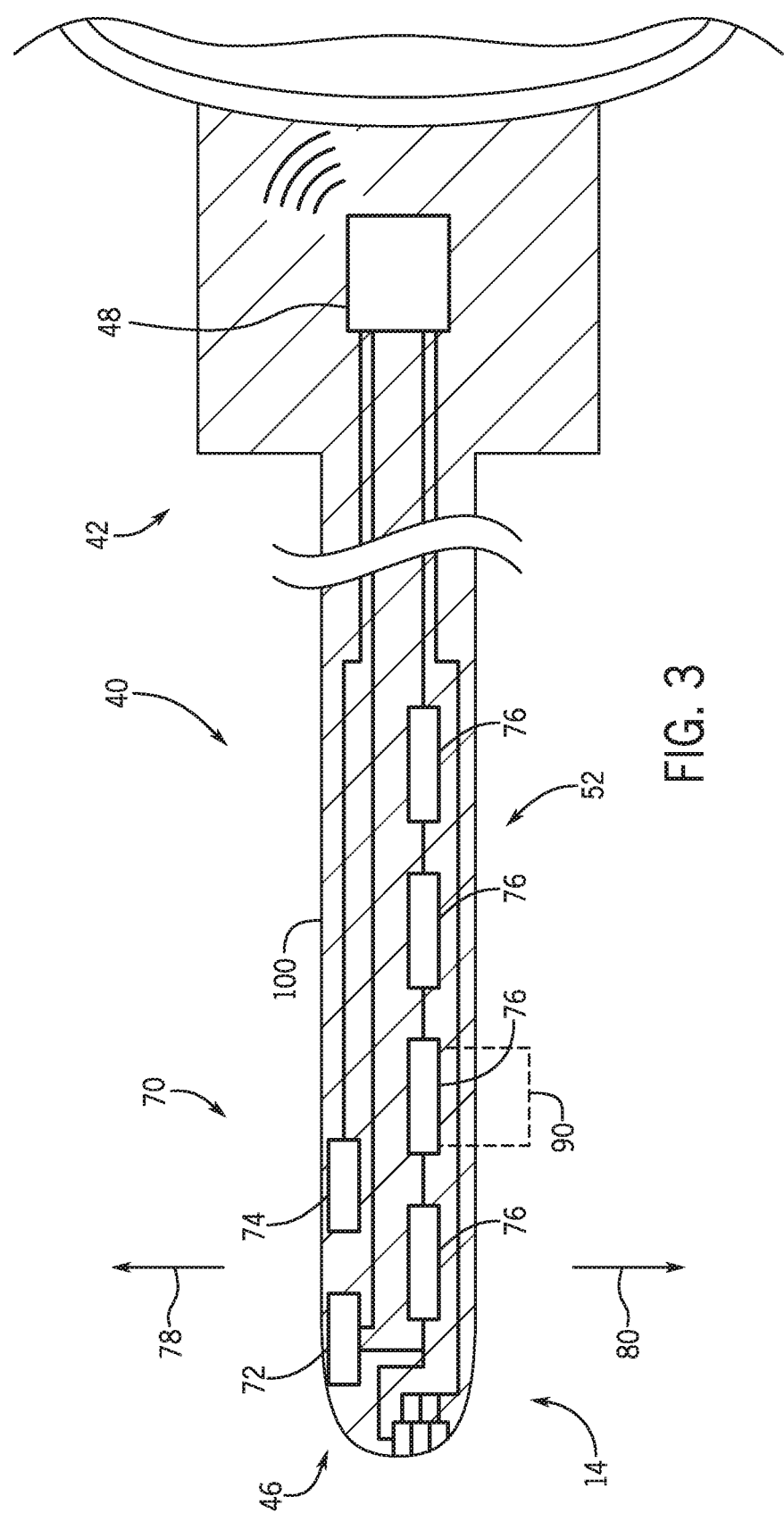
FIG. 3 illustrates a cross-sectional side view of a liquid testing apparatus, in accordance with embodiments described herein.

FIG. 3 illustrates a cross-sectional side view of a liquid testing apparatus 14. As illustrated, the sensors 46 may be embedded within the shaft 40 of the liquid testing apparatus 14. For example, the sensors 46 may be flush with an exterior surface 100 of the shaft 40. By embedding the sensors 46 within the shaft 40, the liquid testing apparatus 14 may facilitate insertion of the shaft 40 into a conduit 16 of the engine 10. Placement of the sensors 46 within the shaft 40 may also reduce contact between the conduit 16 and the sensors 46 during insertion of the liquid testing apparatus 14.

As explained above, the liquid testing apparatus 14 may include a power generator 52 capable of generating power to power the sensors 46 as well as the transmitter 48. For example, one of the sensors 46 may be an optical sensor 70. The optical sensor 70 includes a transmitter 72 (e.g., light emitting diode) and a receiver 74. In operation, the transmitter 72 emits light at one or more wavelengths into the fluid surrounding the shaft 40. As the light contacts the fluid, a portion of that light is reflected and is detected by the receiver 74. The amount of light detected and/or the wavelength of the light detected may then be used to determine characteristics of the fluid (e.g., viscosity, particulate content, fluid level).

In order to power the optical sensor 70 as well as other sensors 46, the liquid testing apparatus 14 includes the power generator 52. In FIG. 3, the power generator 52 includes multiple piezoelectric generators 76. In operation, as fluid moves past the shaft 40 of the liquid testing apparatus 14 (e.g., due to pumping by an oil pump), the shaft 40 may bend and flex in axial directions 78 and 80. The bending and flexing of the shaft 40 mechanically deforms the piezoelectric generators 76 and as the piezoelectric material of the piezoelectric generators 76 mechanically deforms they generate electricity. The liquid testing apparatus 14 then uses this electrical power to power the sensors 46 as well as the transmitter 48. In some embodiments, power generated by the power generator 52 may also facilitate recharging of the vehicle's battery 24 and/or power other components on the vehicle. In some embodiments, the shaft 40 defines/includes a flap 90 that likewise moves in response to the flow of fluid through the engine 10. The flap 90 may couple to one or more piezoelectric generators 52 that then generate electricity as the flap 90 moves and mechanically deforms the piezoelectric material of the piezoelectric generators 52.

Figure 4:
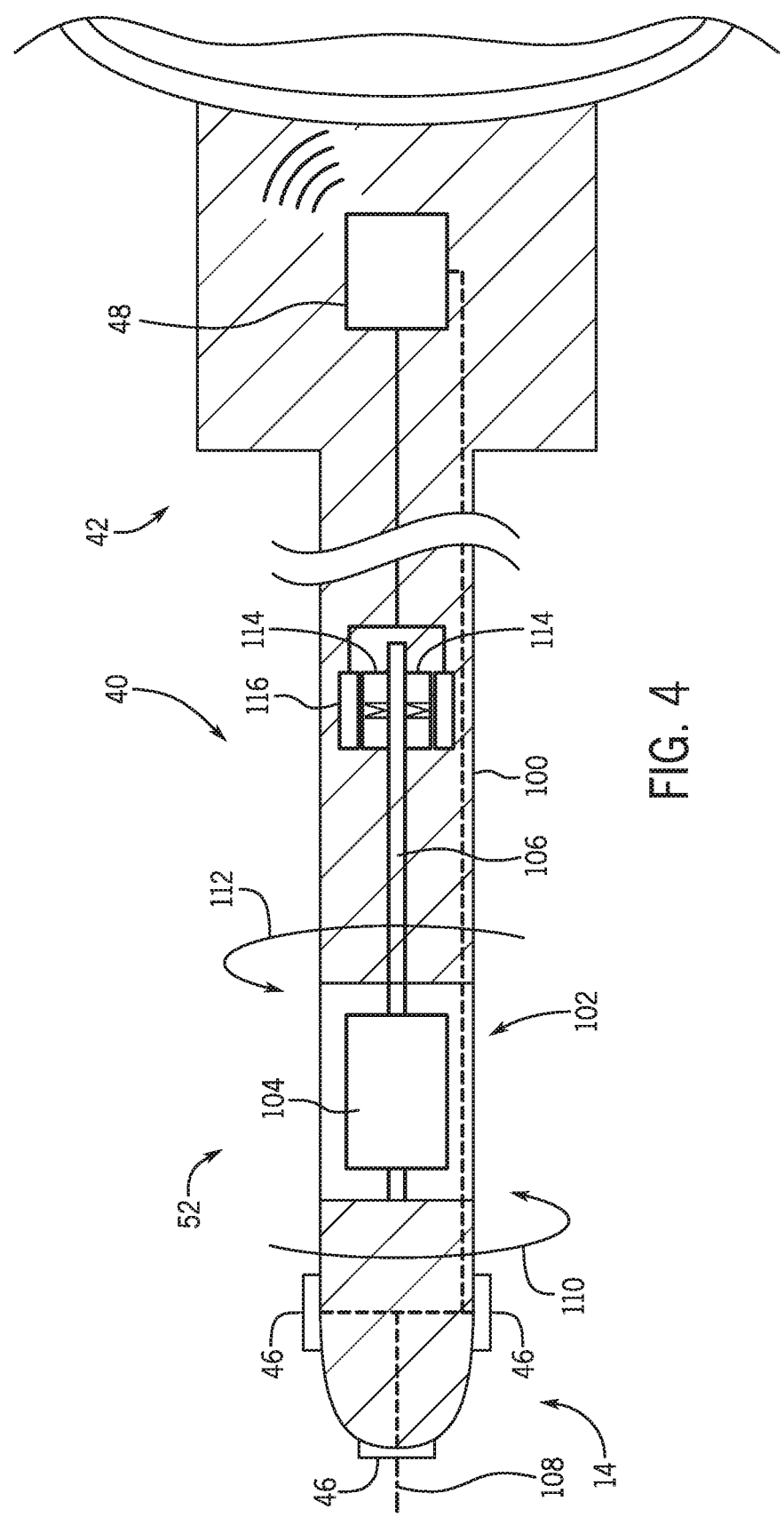
FIG. 4 illustrates a cross-sectional side view of a liquid testing apparatus, in accordance with embodiments described herein.

FIG. 4 illustrates a cross-sectional side view of a liquid testing apparatus 14. In some embodiments, the sensors 46 may be coupled to an exterior surface 100 of the shaft 40, which may facilitate replacement of the sensors 46. As explained above, the liquid testing apparatus 14 may include a power generator 52 capable of generating power to power the sensors 46 as well as the transmitter 48. For example, the shaft 40 may define an aperture 102 that receives blade(s) 104 coupled to a shaft 106. As the fluid pump drives fluid through engine 10, some of the fluid flows through the aperture 102, which contacts the blade(s) 104 causing the blade(s) 104 to spin about the axis 108 of the shaft 40 in circumferential directions 110 or 112. As the blade(s) 104 rotate about the shaft 106, one or more magnets 114, coupled to the shaft 106, rotate within a coil 116 producing electrical power. The liquid testing apparatus 14 then uses this electrical power to power the sensors 46 and the transmitter 48. In some embodiments, power generated by the power generator 52 may also facilitate recharging of the vehicle's battery 24 and/or power other components on the vehicle.

Figure 5:
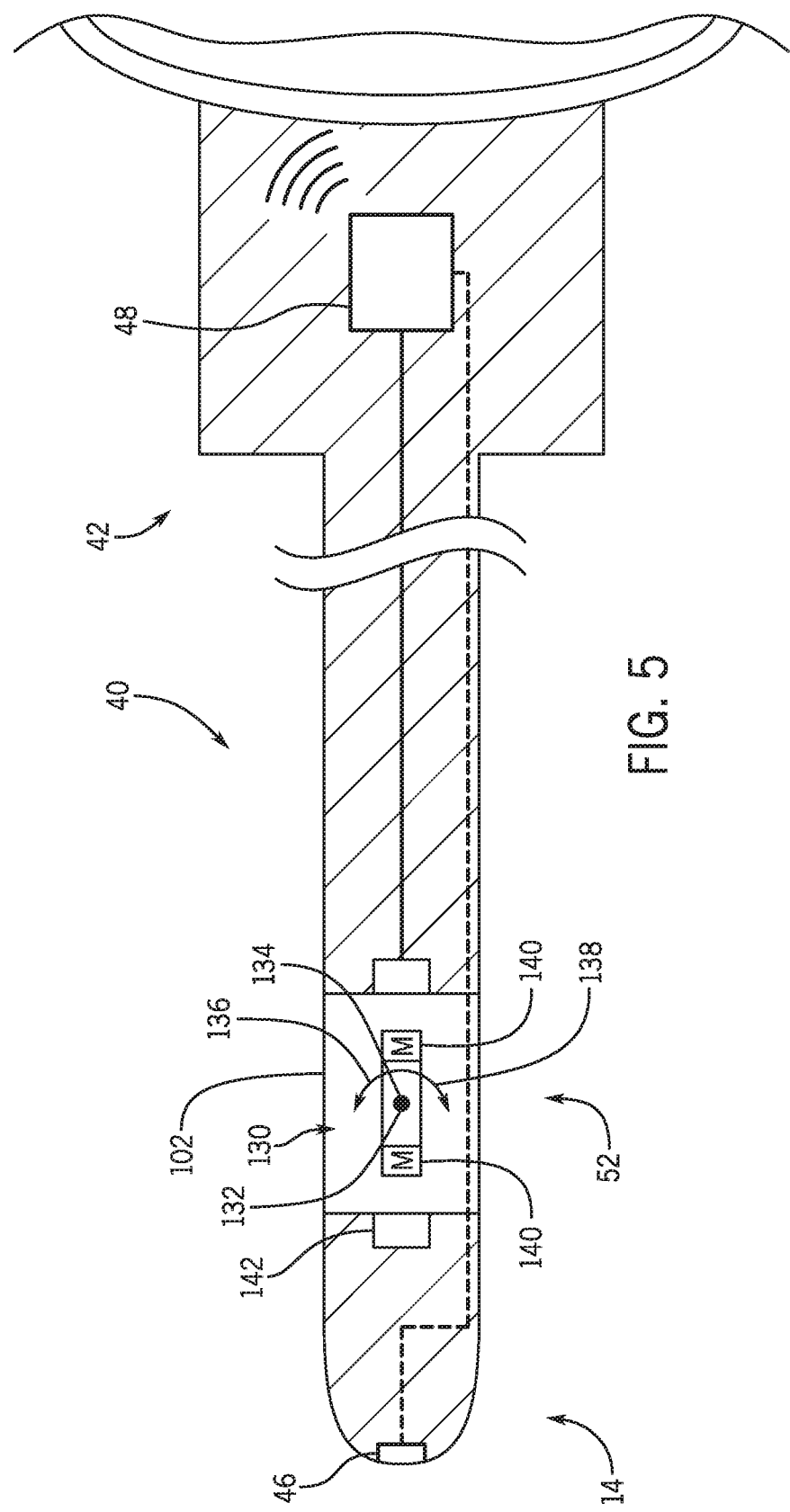
FIG. 5 illustrates a cross-sectional side view of a liquid testing apparatus, in accordance with embodiments described herein.

FIG. 5 illustrates a cross-sectional side view of a liquid testing apparatus 14 with a power generator 52. As illustrated, the shaft 40 may define an aperture 102 that receives a blade 130 coupled to a shaft 132. As the fluid pump drives fluid through the engine 10, it flows through the aperture 102 contacting the blade 130 causing the blade 130 to spin about the axis 134 in circumferential directions 136 or 138. As the blade 130 rotates, it rotates one or more magnets 140 coupled to the blade 130. As the magnets 140 rotate, they generate an electromagnetic field in a coil 142 surrounding the magnets 140, which produces electrical power. The liquid testing apparatus 14 then uses this electrical power to operate the sensors 46 and the transmitter 48. In some embodiments, power generated by the power generator 52 may also facilitate recharging of the vehicle's battery 24 and/or power other components on the vehicle.

The technical effects of the systems and methods described herein include a vehicle liquid testing system that uses a liquid testing apparatus to detect characteristics of a vehicle fluid. The vehicle liquid testing system also includes a controller capable of monitoring those characteristics and advising a vehicle owner and/or mechanic of possible problems. This controller could be integral with the liquid testing apparatus, which may have form factors of a traditional dipstick such that the liquid testing apparatus can be inserted into a dipstick receptacle for retrofitting. Typical form factors of a dipstick are a length between 5 and 24 inches, and a width between 0.02 and 0.3 inches. As noted herein, the liquid testing apparatus 14 may have a dipstick form factor. For example, the shaft 40 may have dimensions corresponding to those of a typical form factor for a traditional dipstick.

As used herein, the terms "inner" and "outer"; "up" and "down"; "upper" and "lower"; "upward" and "downward"; "above" and "below"; "inward" and "outward"; and other like terms as used herein refer to relative positions to one another and are not intended to denote a particular direction or spatial orientation. The terms "couple," "coupled," "connect," "connection," "connected," "in connection with," and "connecting" refer to "in direct connection with" or "in connection with via one or more intermediate elements or members."

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. Moreover, the order in which the elements of the methods described herein are illustrate and described may be re-arranged, and/or two or more elements may occur simultaneously. The embodiments were chosen and described in order to best explain the principals of the disclosure and its practical applications, to thereby enable others skilled in the art to best utilize the disclosure and various embodiments with various modifications as are suited to the particular use contemplated.

The invention claimed is:

1. A vehicle liquid testing system, comprising:
   a liquid testing apparatus with a form factor of a dipstick, wherein the liquid testing apparatus is configured to be inserted into a dipstick conduit of a vehicle, the liquid testing apparatus comprising:
      a power generator configured to generate power;
      a sensor configured to detect a property of a fluid in the vehicle and to emit a signal indicative of the property, wherein the sensor is configured to be powered by the power generator and an external battery positioned outside of the liquid testing apparatus, and wherein the power generator is configured to provide power to the external battery in the vehicle to facilitate recharging the external battery; and
      a transmitter configured to receive the signal from the sensor and transmit the signal.

2. The system of claim 1, comprising a controller configured to receive the signal from the transmitter and to compare the signal from the sensor to a threshold level to determine a condition of the fluid.

3. The system of claim 2, comprising an electronic device communicatively coupled to the controller, wherein the electronic device is configured to receive property data related to the condition of the fluid from the controller and to display the property data.

4. The system of claim 3, wherein the electronic device is a mobile electronic device that is separate from the vehicle.

5. The system of claim 1, wherein the power generator is configured to generate the power using movement of the fluid.

6. The system of claim 5, wherein the power generator comprises a piezoelectric generator.

7. The system of claim 6, wherein the power generator comprises a flap coupled to the piezoelectric generator, and wherein movement of the flap is configured to activate the piezoelectric generator.

8. The system of claim 5, wherein the power generator comprises a blade coupled to a shaft that is coupled to magnets, and the blade is configured to rotate the shaft to thereby rotate the magnets within a coil to generate the power.

9. The system of claim 1, wherein the sensor is at least one of a temperature sensor, a fluid level sensor, a viscosity sensor, a flow rate sensor, a chemical sensor, and a particulate sensor.

10. The system of claim 1, wherein the fluid comprises motor oil, automatic transaxle oil, coolant, power steering fluid, or brake fluid.

11. A vehicle liquid testing system, comprising:
a liquid testing apparatus with a form factor of a dipstick, comprising:
a sensor configured to detect a property of a fluid in a vehicle and to emit a signal indicative of the property;
a power source comprising one or more power generators configured to provide power to the sensor and to an external battery in the vehicle to facilitate recharging the external battery;
a transmitter configured to receive the signal from the sensor and transmit the signal; and
a controller configured to receive the signal from the transmitter, and to compare the signal from the sensor to a threshold level to determine a condition of the fluid.

12. The system of claim 11, wherein the power generator comprises a piezoelectric generator.

13. The system of claim 11, wherein the power generator comprises a blade configured to cause relative rotation between magnets and a coil to generate power.

14. The system of claim 11, wherein the sensor comprises a temperature sensor, a fluid level sensor, a viscosity sensor, a flow rate sensor, a chemical sensor, a particulate sensor, or a combination thereof.

15. A liquid testing apparatus with a form factor of a dipstick, comprising:
a housing comprising:
a sensor within the housing, wherein the sensor is configured to detect a property of a fluid in a vehicle and to emit a signal indicative of the property;
a controller within the housing, wherein the controller is configured to receive the signal from the sensor and to compare the signal from the sensor to a threshold level to determine a condition of the fluid; and
a power source within the housing, wherein the power source is configured to power the sensor, the controller, or both, and wherein the power source is configured to provide power to an external battery in the vehicle to facilitate recharging the external battery.

16. The apparatus of claim 15, wherein the power source comprises a power generator configured to generate power using movement of the fluid in the vehicle.

17. The apparatus of claim 16, wherein the power generator comprises a piezoelectric generator.

18. The apparatus of claim 15, wherein the sensor comprises a temperature sensor, a fluid level sensor, a viscosity sensor, a flow rate sensor, a chemical sensor, a particulate sensor, or a combination thereof.

19. The apparatus of claim 15, comprising a transmitter within the housing, wherein the transmitter is configured to receive the signal from the sensor and to transmit the signal to an electronic device that is external to the liquid testing apparatus with the form factor of the dipstick.

20. The apparatus of claim 15, wherein the controller is configured to provide an alert based on the condition of the fluid.

* * * * *